United States Patent [19]

Nguyen

[11] 4,240,284
[45] Dec. 23, 1980

[54] METHOD AND APPARATUS FOR DETERMINING THE TEMPERATURE OF THE CONDENSATION POINT OF A SUBSTANCE

[75] Inventor: Van L. Nguyen, Antony, France
[73] Assignee: Sereg, Montrouge, France
[21] Appl. No.: 63,630
[22] Filed: Aug. 3, 1979
[51] Int. Cl.³ .............................................. G01N 25/12
[52] U.S. Cl. .................................................. 73/17 A
[58] Field of Search ..................... 73/17 R, 17 A, 29
[56] References Cited
U.S. PATENT DOCUMENTS

| 3,195,344 | 7/1965 | Francisco | 73/17 A |
| 3,623,356 | 11/1971 | Bisberg | 73/17 A |

Primary Examiner—Donald O. Woodiel
Attorney, Agent, or Firm—Mikio Ishimaru; Joseph J. Kaliko; Dale V. Gaudier

[57] ABSTRACT

The temperature of the condensation point of light hydrocarbons in a gas is quickly determined by heating a frosted mirror placed in a gas swept enclosure up to the evaporation temperature of all the heavy and light hydrocarbons. The mirror is first cooled as quickly as possible to a temperature higher than the presumed condensation temperature for the light hydrocarbons. Then is cooled much more slowly until the appearance of the first condensations on the mirror. Another cycle as described above is started, in which the presumed condensation temperature value is taken as being equal to the condensation start temperature value of the previous cycle.

25 Claims, 7 Drawing Figures

METHOD AND APPARATUS FOR DETERMINING THE TEMPERATURE OF THE CONDENSATION POINT OF A SUBSTANCE

This invention relates to devices for determining the condensation temperature of a vapour of a fluid contained in a gas.

These devices are usually designated by technicians as hygrometers. Such a hygrometer essentially comprises of a mirror disposed within an enclosure through which the gas containing the vapour of the fluid whose condensation temperature has to be determined is arranged to flow, a light source for producing a beam of light directed onto the mirror, one or several photocells positioned in relation to the mirror in such a way as to receive the light diffused by the mirror and lastly means for controlling the temperature of the mirror, these means being controlled from signals delivered by the photocells.

The means most currently used to maintain the temperature of the mirror of a hygrometer are on one hand a cold source, generally consisting of Peltier effect elements, and a heat source consisting of one or more resistance heating elements. The hygrometer structure described above is the most general one. However, depending on the fluid types to be measured, differences can exist, in particular as to the structure of the mirrors. For example, when the fluid vapour is a product such as water, the mirror consists of a polished surface, for instance a reflecting layer of gold. When the water condenses on the polished surface, the mirror becomes a diffusing mirror which sends back part of the light by diffusion; and in this case, the photocells are placed so as to receive the diffused light and on no account the reflected light. On the other hand, when the condensates are fluids such as hydrocarbons, they condense for forming droplets which, when they coalesce, produce a reflecting surface, so that in this case, the mirror used is a frosted mirror. When the hydrocarbons condense on such a mirror, they render it reflective, and as a result, the incident light, instead of being diffused by the frosted mirror as in the absence of condensate, is reflected by a polished surface consisting of a film of hydrocarbons. In every case, each time the light beam passes from the reflection state to the diffusion state or inversely, the light sensitive photocells deliver at their outputs an electric signal which passes from a first level to a second level. The passage from one level to another corresponds to the beginning of the fluid's condensation on the mirror.

A hygrometer, as described above, operates as follows: the mirror, regardless of its surface state, is first subjected to a relatively elevated temperature. Then the temperature is slowly reduced until the first condensates appear. The appearance of these condensates automatically entails for the light returned by the mirror a passage from one state to another, for example from the reflection to the diffusion state. This passage is detected and interpreted by the photosensitive cells, which deliver at their outputs a signal passing from a first level to a second level. This variation in the signals delivered by the photosensitive cells is analysed by means, usually electronic, which control both sources, of heat and cold respectively, to maintain the mirror temperature at the temperature of the onset of the condensation of the fluid vapour contained in the circulating gas which is flowing over the mirror surface. A temperature sensor consisting for example of a thermocouple, continuously outputs the temperature of the mirror, which can be, for instance, recorded, so that the technicians can know it at any time and draw conclusions from it as to the hygrometric degree of the fluid contained in the gas and thereby the value of the concentration of these fluids contained in the gas passing through the hygrometer.

In the particular case of hydrocarbons, it is quite obvious that the carrying gases, in particular methane, ethane, etc. also carry so-called heavy hydrocarbons, even if they are in much smaller quantities than light hydrocarbons. These heavy hydrocarbons are deposited by attaching themselves, but very slowly, onto the mirror. As a result, the signals delivered by the cells are no longer representative of the initial condensation of the vapours of the main fluids found in the circulating gas, and the hygrometer then delivers incorrect results which are reflected, as shown by experience, in a drift of the signals.

It is therefore necessary to calibrate the hygrometer periodically; this corresponds to a cleaning of the mirror. The most currently used process for cleaning a mirror consists in heating it to a temperature significantly higher than the vaporisation temperature of all the condensates likely to be found in the circulating gas, and in purging the enclosure with the gas to eliminate all the vapours of the different products, whether light or heavy hydrocarbons. Of course, the purging can also be done with a gas of another type than the gas to be analysed, for example a neutral gas. Then, when the enclosure and the mirror are thought to be perfectly cleaned of all the condensates, the mirror temperature is reduced as described above, until the appearance of the first condensate. This is regulated as described above to the initial condensation of the main products contained in vapour form in the gases passing through the hygrometer.

This type of calibration, or more particularly cleaning of the mirror, can be carried out for example at half-hourly or hourly intervals. This process gives very good results, regardless of the nature of the condensates which might have deposited themselves on the mirror.

On the other hand, this process presents major disadvantages in the case of the detection of light hydrocarbons in a gas containing traces of heavy hydrocarbons.

Thus, in this case, after cleaning the mirror as described above, the mirror temperature is lowered to bring it towards the presumed condensation temperature range of the light hydrocarbons. Nevertheless, due to inertia, this temperature usually falls below the condensation temperature before the heat and cold sources can be controlled to obtain the regulation of the mirror temperature at the initial condensation point. Thus, from a temperature point that is lower than the initial condensation temperature, it is observed that in cases of gases carrying all kinds of hydrocarbons, the mirror temperature cannot stabilize on the initial condensation temperature, but drifts substantially, usually increasing definitely beyond that temperature at which it should stabilize itself, that is to say at the temperature of initial condensation of the light hydrocarbons, large quantities of which are usually contained in the carried gas.

This phenomenon is very inconvenient, as it does not allow very easy detection of the dew point temperature of the light hydrocarbons which form the majority of the gases to be analysed.

This phenomenon has been observed by the applicant and the applicant has observed that this phenomenon was mainly due to the few heavy hydrocarbon traces always present with light hydrocarbons, even when the latter are in very much in the majority.

The applicant also observed that heavy hydrocarbons are deposited slowly but continuously on the frosted mirror as their condensation temperature is greater than that of light hydrocarbons. Thus, these heavy hydrocarbons tend to make the mirror reflective and the heavy hydrocarbon deposits are interpreted as a condensation of light hydrocarbons. The mirror, now reflective with a layer of heavy hydrocarbons, reflects the incident light on the photosensitive photocells which deliver at their outputs a signal which is interpreted as a control signal for the reheating of the mirror. This signal is emitted until, theoretically, all the hydrocarbons which might have deposited themselves have evaporated. But, as these products are heavy hydrocarbons, the evaporation temperature is very high and is especially significantly higher than that at which the mirror should stabilize itself, that is to say the evaporation temperature of the light hydrocarbons. This is the phenomenon observed, that is to say, a mirror temperature rising more and more to values which are in no case significant. The temperature does not usually stabilize itself, as the hygrometer's logic commands another heating of the mirror to clean it correctly, as described above, before the mirror temperature has stabilized at the temperature of the beginning of the condensation of any product.

Therefore, users of such a hygrometer see temperature charts on the recorders, such as that displayed in FIG. 1. On this figure, there is more particularly shown a period of heating the mirror at a very high temperature, for example up to the temperature $\theta_1$ for a given time up to $t_1$; from this moment $t_1$, the mirror temperature has dropped for a certain period until the appearance of the first condensates on the mirror, for instance up to instant $t_2$. From this instant, the mirror heating command is effected but, due to the heat inertia, the mirror nevertheless continues to cool slightly down to a temperature $\theta_2$, lower than the temperature $\theta_3$ which marks the commencement of condensation of the light hydrocarbons on the mirror. From the time when the mirror temperature has reached temperature $\theta_2$, the mirror starts to warm up. It is noted however, that as described hereinbefore, the temperature rises uniformly up to, for instance, a temperature $\theta_4$ very clearly higher than the temperature $\theta_3$, which should be the temperature at which the mirror should maintain itself; that is to say, the temperature of the commencement of condensation of the light hydrocarbons which are generally in the majority. This temperature should stabilize fairly rapidly after a few oscillations, as shown by the dotted lines in FIG. 1. At instant $t_3$, the hygrometer's logic controls the warming of the mirror to the temperature $\theta_1$ and its purging for a time included between $t_3$ and $t_4$. From $t_4$, the process repeats itself periodically as stated above.

It therefore appears that with such a hygrometer, it is impossible to obtain results that are easily exploitable and usable for technicians who do not have the means and/or the time to interpret very finely the results given by such a hydrometer. In fact, it would nevertheless be possible to obtain a measurement by extrapolating the instant at which the mirror temperature starts to decline after the first few condensates have deposited themselves on the mirror, that is to say the value of temperature $\theta_3$ represented by a variation of the downward curve determined in the figure by instant $t_2$.

To sum up, the fault of hygrometers currently available for hydrocarbons derives from the attempt to regulate the mirror temperature on a thickness of condensate, which is virtually impossible in the case of light hydrocarbons containing traces of heavy hydrocarbons.

The purpose of this invention is to implement a process and a device for determining the condensation temperature of the vapour of a fluid, as for example light hydrocarbons, carried in a gas with heavy hydrocarbons, to give indications that can be easily interpreted by technicians and above all are meaningful at each instant.

More particularly, this invention finds an advantageous application in the case of slowly evolving processes such as those found in the treatment processes for natural gases mainly containing methane (CH4), as these gases carry a large majority of light hydrocarbons, but also a percentage, which can be low, of heavy hydrocarbons whose condensation temperature is clearly higher than that of the light hydrocarbons.

More precisely, the subject of this invention is a process for determining the temperature of the condensation point of a substance such as hydrocarbons in a gas that may contain a low percentage of heavy hydrocarbons, characterized by the fact that it consists in performing a cycle comprising:

the heating of a frosted mirror placed in a swept enclosure up to a temperature at least equivalent to the evaporation temperature of all the heavy and light hydrocarbons for the conditions concerned, a cooling during a first time period of the said mirror as quickly as possible, to a temperature similar to but higher than the presumed condensation temperature for the said light hydrocarbons, and in a second time period continuing on from the first time period, a continuous cooling of the said mirror, but much more slowly than during the said first time period until the appearance of the first condensations on the said mirror, and the memorisation of the value of the said condensation start temperature, and effecting, following the appearance of the said condensation, another cycle as described above, in which the presumed condensation temperature value is taken as being equal to the condensation start temperature value memorised in a previous cycle.

Another subject of this invention is apparatus for determining the temperature of the condensation point on a mirror of a substance such as hydrocarbons in a gas that can contain heavy hydrocarbons, characterized by the fact that it comprises means for controlling the temperature of the said mirror, means for measuring the temperature of the said mirror, means for detecting the first condensates on the said mirror, a logic circuit cooperating with the said means for controlling the temperature of the mirror, means for detecting the appearance of the first condensates on the mirror, means for measuring the temperature of the said mirror, the said logic circuit being capable of controlling a temperature cycle of the mirror between at least a first and a second temperature, the said cycle having two speed of variation of the mirror temperature, the changing of the variation speeds being effected as a function of the presumed condensation temperatures of the said vapours measured in a preceding cycle.

Other characteristic and advantages of the present invention will appear in the course of the following description given with reference to the attached drawing, in which.

Figure 1:
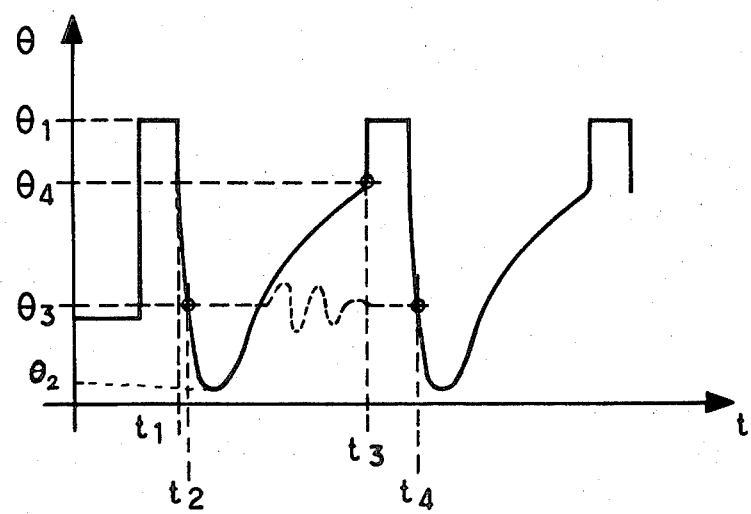
FIG. 1 is a curve showing a prior art hygrometer temperature chart curve.
Figure 2:
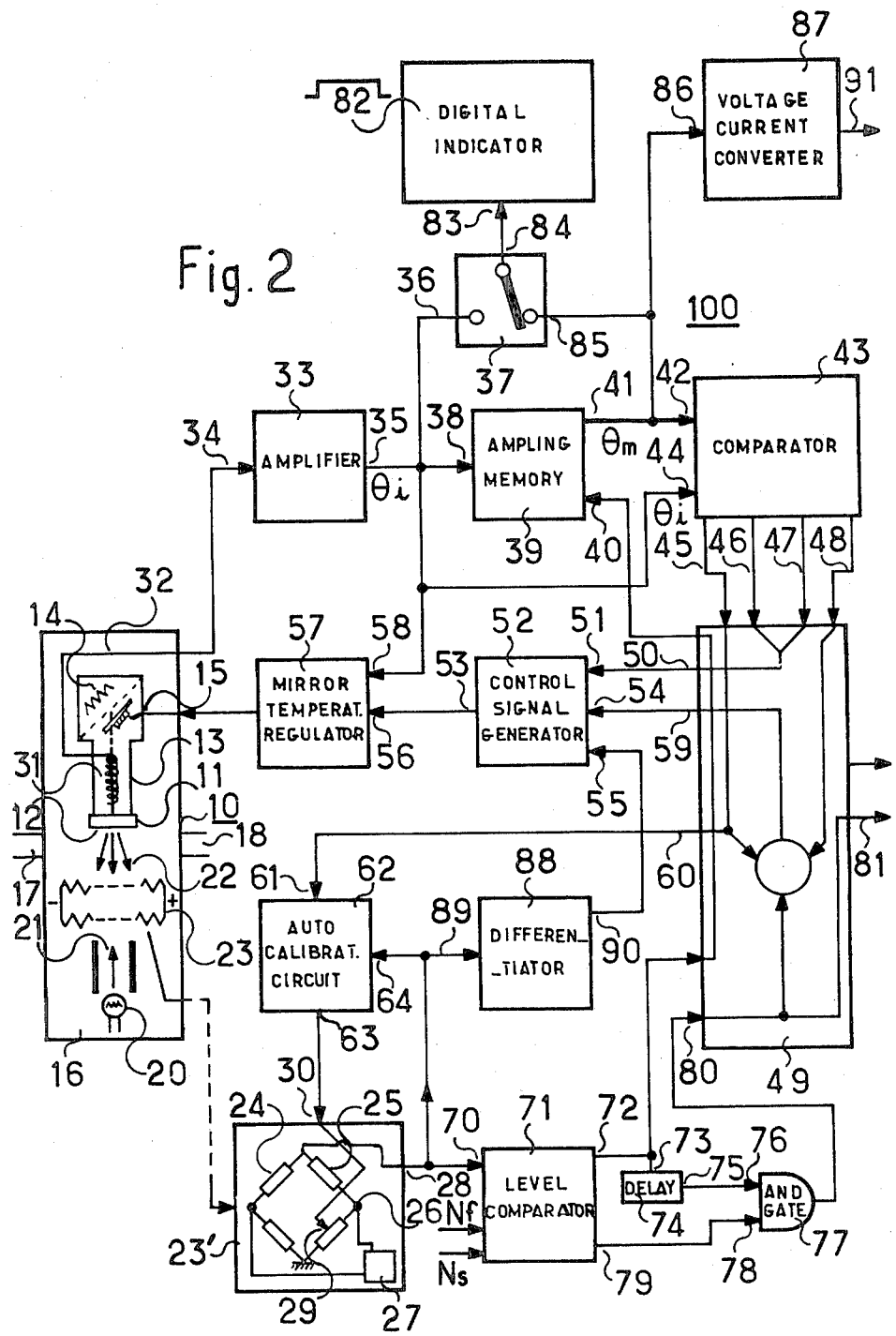
FIG. 2 represents in the form of a block diagram an embodiment of a dew point hygrometer in its application specific to the measurements of condensation temperatures of light hydrocarbons carried by a gas.

FIG. 2 represents, in block diagram form, an embodiment of a dew point hygrometer in its particularly advantageous application to measurements of the condensation temperature of light hydrocarbons carried by a gas, which can also contain heavy hydrocarbons. The embodiment shown applies more particularly in the case of slowly evolving processes. Although this embodiment is particularly advantageous in this case, it can nevertheless be applied, with slight modifications in its structure and without departing from the framework of the invention, to the determination of the condensation point of water or of a similar liquid; the only essential modification to be made to such a hygrometer is mentioned below, but nevertheless this modification essentially concerns only the surface of the mirror on which are to be deposited the condensates and the different operating parameters which are generally inherent in the materials whose condensation temperature is to be measured. These modifications can also concern, without it being necessary, the arrangement of the photocells in relation to the condensation mirror.

The embodiment of the hygrometer shown in FIG. 2 consists of a head 10 in which is disposed a mirror 11, generally with a frosted surface 12 forming a diffuser. With this mirror 11 is associated a temperature regulating unit 13, comprising essentially heating means 14 and cooling means 15. The heating means are generally implemented as heating resistances fed with electric power and the cooling means are generally Peltier effect elements, fed by a controllable electric power source. The heating and cooling means are associated with the mirror 11 in a way known in the field of hygrometer techniques.

The mirror 11 is positioned in an enclosure 16 comprising an inlet 17 and an outlet 18. This enclosure 16 can be swept by the fluid or the gas of which it is desired to measure the dew-point temperature, that is to say the percentage, in this illustrated example, of hydrocarbons contained in the gas passing through chamber 16.

In this head 10 is also fitted a light source 20 connected to means for focussing the light beam 21 on the mirror 11. The light 22 diffused by the surface 12 of this mirror is received by optical sensors 23 consisting mainly of photocells 24 and 25 arranged in a Wheatstone bridge 26. For convenience of illustration in the figure, the optical sensor unit 23 is included and illustrated diagrammatically in the square block 23', which shows the Wheatstone bridge 26, its power supply 27 and the two photocells 24 and 25 respectively, each in one branch of the bridge. The output signal at the terminals of the Wheatstone bridge 26 can be similarly received and relayed by an amplifier, making it possible to deliver to output 28 a signal whose use will be explained hereinafter. Similarly, in this block 23' is shown diagrammatically a means making it possible to balance this bridge; this means, referenced 29, is illustrated by a potentiometer 29, which will preferably consist of electronic means controllable by an electrical signal applied to the control input 30. These means are well known in this field and will not be described in greater detail.

The head 10 of the hygrometer also embodies a temperature sensor 31 placed as close as possible to the mirror 11 in order to determine its temperature at any instant. The output 32 of this temperature sensor 31 is connected to the input 34 of the amplifier 33.

The amplifier 33 delivers at its output 35 an electrical signal representing the instantaneous value of the temperature of the mirror 11 detected by the sensor 31. The output 35 of amplifier 33 is connected to a first input 36 of a selector switch 37; this output 35 is also connected to input 38 of a controllable sampling memory 39 which can be controlled by an electrical signal applied to its control input terminal 40. The sampling memory 39 makes it possible, under the control of an electric signal applied to its input 40, to keep in memory the value of the signal which was applied to its input 38 at at the instant determined by the control signal and, without another control order, to store indefinitely this value of the temperature which has been memorised.

This temperature, memorised in the form of an electric signal $\theta m$, can be obtained at the output 41 of the sampling memory 39. The output 41 of the sampling memory 39 is connected to a first input 42 of a four-level comparator 43. The second input 44 of this comparator 43 is connected to the output 35 of the mirror temperature amplifier 33 delivering at its output 35 the signal $\theta i$ representing the value of the temperature of mirror 11 at each instant. This four-level comparator is capable of comparing the signal $\theta i$ delivered at the output 35 with four values, in the example illustrated $T_1, T_2, T_3$ and $T_4$.

These four values represent temperature levels which can be predetermined or adjusted as required. Thus, $T_1$ is a predetermined relatively high temperature representing a value of the temperature that is substantially higher than the value of the vaporisation temperature of all the products capable of being deposited on the mirror contained in head 10 of the hygrometer. The temperature $T_4$ is a much lower temperature than the condensation temperature of products likely to be in vapour form in this same gas. On the other hand, the two intermediate temperatures $T_2$ and $T_3$ are determined as a function of the signal $\theta m$ delivered at the output of the memory 39. As an example, the value $T_2$ represents a value of the temperature equivalent to the value of the temperature $\theta m$ that is memorised, to which is added a certain value representing a certain temperature range which is determined as a function of the different parameters. This range can be, for example, about 2 to 3 degrees Centigrade. Thus, the value of the temperature $T_2$ can be equal to $\theta m + 3°$ C. Similarly, the temperature $T_3$ is a temperature determined as a function of this same temperature $\theta m$ obtained at the output of the sampling memory 39, less a certain value representing a certain temperature range which can also, for example, be equal to 2° or 3° C. In this case, temperature $T_3$ is equal to θ m−3° C. The comparator 43 in this embodiment, given that the temperature can only be found within the two extreme limits T₁ and T₄, has only four outputs, 45, 46, 47 and 48, making it possible by logic signals, for example two state signals represented respectively by 0 and 1, to determine whether the temperature $\theta$ i, that is to say the temperature of the mirror, is less than or equal to $T_1$, but greater than $T_2$ and so on up to $T_4$, given that $\theta$ i cannot be less than $T_4$. These four outputs of the four-level comparator 43 are connected respectively to four corresponding inputs of a logic system 49 which can be for example a part of a microprocessor like those available currently in the trade and which can have different structural forms depending on the manufacturer. The logic of such a system does not present any difficulty for manufacturers, it will be possible to implement it by referring to the different functions explained below.

A first output 50 of the logic system 49 is connected to a first input 51 of a control signal generator 52, capable of delivering at its output 53 a signal depending on the control orders to be applied to its inputs, in particular the first input 51 but also the second input 54 and the third input 55. The signal produced by the control signal generator 52 at its output 53 is applied to a first input 56 of a mirror temperature regulator 57 whose second control input 58 is connected to the mirror signal amplifier output 33 which delivers the signal $\theta$ i. The second output 59 of the logic system 49 is connected to the second input 54 of the control signal generator 52. The third output 60 of the logic system 49 is connected to a control input 61 of an automatic calibration device 62, causing it to produce at its output 63 a control signal for a given time to control, by way of the input 30 mentioned hereinbefore, the balancing of the optical sensor before it can carry out the measurement. The balancing is effected by balancing the Wheatstone bridge shown diagrammatically in block 23′, for example under the action of the command signal delivered by the logic system at its output 60 and applied to the input of the automatic calibration device; the latter delivers a signal during a time period, for instance, one second which enables the Wheatstone bridge to balance itself so as to produce at its output a signal representing a level of zero. This calibration operation, being automatic, goes on operating as long as the signal produced at its output 28 has not reached its logic value zero. For this purpose, the output 28 of optical sensor 23′ is connected to the control input 64 of the automatic calibration 62 in the manner of a servo-control.

Figure 4:
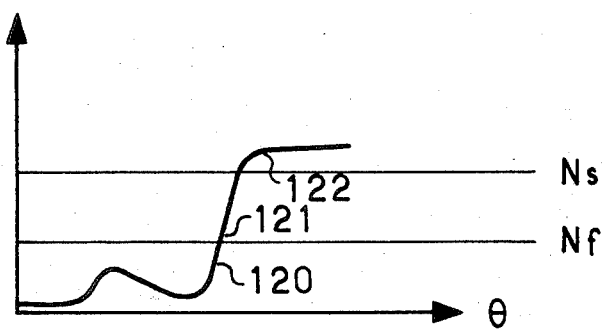
FIG. 4 is a curve representing the output signal of the photosensitive cells of FIG. 2, and FIG. 5, A and B, represents two comparative curves illustrating the different measurement recordings made with a hygrometer according to the embodiment of FIG. 2.

The output 28 of the optical sensor is also connected to an input 70 of a comparator with two predetermined levels 71, these two levels being respectively $N_s$, called the supervisory level, and a predetermined level $N_f$, called the operating level. These two levels are illustrated on the curve of FIG. 4. This FIG. 4 shows the signal produced at the output of the optical sensor when the first condensates appear on the mirror. The part of the signal 120 shown below the line and illustrating the value of the signal $N_f$ (operating value), is considered as a level zero signal, that is to say a signal with a very low level, the only variations being due to well known spurious variations, in particular in the baselines of signals delivered at the output of the sensors consisting mainly of Wheatstone bridges. The two-level comparator 71 compares the signal applied to its input 72 in relation to its two predetermined values $N_s$ and $N_f$. The value $N_f$ signal represents a level which, when passed by the signal applied to the input 70, determines that condensations have appeared on mirror 11 and that the optical sensor has therefore tripped to deliver at its output a signal of a value that is substantially greater than the reference value taken as being value zero. This sudden variation of the signal delivered by the sensor is illustrated in FIG. 4 by the variation of the value of the signal, and in particular in the part of the curve identified as 120, to arrive then at a value 121 corresponding to the appearance of an incipient condenstion on the mirror and therefore a possibility of determining the mirror temperature corresponding to the condensation.

To do this, as soon as the signal has reached a certain value such that 121 has in particular passed operating level $N_f$, a signal is sent by output 72 of level-comparator 71, through the logic system 49, to the input 40 of the sampling memory, which then commands at this instant the memorisation of the value of the temperature $\theta$ i obtained in the form of a signal at the output 35 of amplifier 33.

The level $N_s$, illustrated in FIG. 4, corresponds to a supervisory level in order to determine whether the signal delivered by the sensor is sufficient to be capable of interpretation as a condensation signal and not as a signal corresponding to dirt or to spurious effects, in particular at the mirror. To this end, in a first embodiment, the output 72 of the two-level comparator 71 is connected to an input 73 of a delay circuit 74 whose output 75 is connected to a first input of an AND gate 77, while the second input 78 of the gate 77 is connected to the output 79 corresponding to the output of the comparator providing the result of the comparison of the signal applied to its input 70 in relation to the predisplayed threshold value $N_s$. Thus, if at the instant when the delay circuit delivers its logic signal, 1 for example, at its output after a certain time determined by the delay circuit 74, whose delay value will be determined by experience, the signal applied to input 70 has not passed the supervisory level $N_s$, that is to say, the two inputs 76 and 78 of gate 77 receive respectively logic signals 1 and 0, the gate 77 then delivers at its output a logic order equal to zero which, through the logic 49, can result in a pre-alarm at output 81. On the other hand, if after the time determined by the delay circuit 74, a logic 1 is applied respectively to the two inputs 76 and 78 of the AND gate 77, there then appears at the output of this latter a signal of logic state 1 which confirms that the hygrometer is working correctly.

The signals emitted at the output 81 are representative of the quality of the hygrometer head and, for example, the production of the "prealarm" means that the mirror has to be replaced or cleaned as has already been described or else that the photocells have undergone an ageing which calls for their replacement.

Generally speaking, any signal appearing at output 81 makes it possible to determine that the hygrometer is not in proper working order and calls for an intervention by a technician to restore it to a correct condition, this signal being maintained if appropriate by a bistable circuit.

The embodiment which has just been described may not give full satisfaction. Thus, when the first few condensates appear, the mirror temperature goes back up to the temperature determined as $T_1$, and the condensates can no longer form on the mirror. The signal delivered then by the cells 23 drops toward the lower values without reaching the supervisory level $N_s$, resulting at each cycle in triggering the "prealarm", which no longer has any significance.

To overcome this indeterminacy, it is necessary that the supervisory level $N_s$ be very close to the operating level, hoping that the inertia of the cooling is relatively substantial to bring sufficient condensates onto the mirror and give rise to a signal delivered by the sensors, of a sufficient level to pass the supervisory level $N_s$. But in the latter case too, these conditions are very uncertain and the prealarm has also not very much significance.

The embodiment which will be described below makes it possible to obtain results which are valid and representative of the aims which are sought in providing an alarm and a prealarm.

This particular embodiment is not specifically illustrated in the drawings but can nevertheless be very easily understood in the light of the description to follow, with reference nevertheless to FIG. 2. In this embodiment, the outputs 72 and 79 of the two-level comparator 71 are connected to two inputs of the logic system 49 which is capable of controlling the following operations.

When the first condensates appear, that is to say when the detector signal goes beyond the operating level $N_f$, the mirror temperature is memorised as already described. This memorisation occurs in the sampling memory 39 in response to a control signal which is applied to it at its control input 40.

As soon as these first few condensates had appeared on the mirror in the previously given method of implementation, the mirror temperature went up almost immediately. In contrast, in this present method, the logic system 49 continues to produce a control signal via the control signal generator such that the mirror temperature cotinues to drop until the temperature of the end of the range in which the first condensates appeared, for example the temperature $T_3$ if the condensates appeared between $T_1$ and $T_3$. By thus continuing to lower the mirror temperature to the end of the range, it is hoped to have sufficient condensate thickness on the mirror for the signal delivered by the optical sensor to be able to reach the value shown at 122 in FIG. 4, and thus to exceed the supervisory level $N_S$.

The logic system 49 determines the instant at which the mirror temperature reaches the temperature range as defined above. At this instant, the two-level comparator 71 delivers at its output 79 a signal representative of the value of the signal delivered by the optical sensor. In the event that the signal delivered by the sensor has not exceeded the supervisory level $N_s$, the logic system then delivers at its output, for example at its output 81, a signal corresponding to a "prealarm". This "prealarm" indicates that the condensates have been detected since the signal has gone beyond the operating value $N_f$, but that the sensor signal is weak since it has not gone beyond the supervisory level $N_s$. This "prealarm" therefore indicates to the users of these hygrometers, for example that they must intervene to check the operation of the hygrometer and, for example, change a few main components such as the mirror or the light sources which no longer have sufficient brightness.

On the other hand, it can happen—as already stated—that condensates do not form in the range included between temperatures $T_2$ and $T_3$. If the condensates appear in a range other than that included between $T_2$ and $T_3$, the hygrometer operates in the same way, that is to say, the mirror temperature is each time brought to the lowest temperature of the range over which these condensates appeared and the various recordings are made in the same way as that described above. It can even happen that they do not appear at all between the temperatures $T_1$ and $T_4$. In this case, if the mirror arrives at the lowest temperature, that is, the temperature $T_4$, and no condensate has formed, the signal delivered by the sensor cannot go beyond the operating level $N_f$. This is interpreted by the logic system 49, which determines that on a complete cycle the signal delivered by the sensor has not exceeded the operating level $N_f$ once; and then this system gives an alarm signal indicating to the users that something has not operated correctly, either in the hygrometer or at the level of manufacture of the gas whose degree of humidity is to be monitored.

The hygrometer can also embody a digital indicator 82, the input 83 of which is connected to the mid-point 84 of selector switch 37 to make it possible to take, at will, either the value of the measurement $\theta i$ delivered at output 35 of the amplifier of the mirror 33, which represents the temperature variations of the mirror at each instant, or the value of the temperature memorised as indicated above, since the second input 85 of selector switch 37 is connected to the output 41 delivering signal $\theta$ m of the sampling memory.

This latter temperature $\theta$ m̂ represents the value of the initial temperature of condensation of the hydrocarbons on the mirror.

The output 41 of the sampling memory can also be connected to an input 86 of a voltage-current converter 87, to deliver at its output an electrical signal in the form of an electric current which will eventually make is possible to control different systems making it possible to act of the quantity of hydrocarbons, in particular light hydrocarbons, contained in the gas. Thus, such a hygrometer can be incorporated in a control loop.

Furthermore, and advantageously, the embodiment shown in FIG. 2 can include a differentiator 88 whose input 89 is connected to output 28 of the optical sensor 23 (or 23'), and whose output 90 is connected to the third input 55 of the control signal generator 52.

This differentiator is used, as a function of the variation of the signal obtained at the output of optical sensor 23 (23'), that is to say when the signal represents a high variation, such as the variation shown at 120 in FIG. 4, to control the control signal generator so that it delivers at its output 53 a signal making it possible to control the mirror temperature variation speed from the instant when the optical sensor has detected a commencement of condensation in mirror 11. Generally, no signal delivered at output 90 commands the reduction in the mirror cooling speed even more than when the mirror temperature has exceeded, in the cooling direction, the temperature $T_2$ defined and mentioned above. This additional characteristic is used to home in with more precision on the temperature of the commencement of condensation of the light hydrocarbons on mirror 11.

Figure 3:
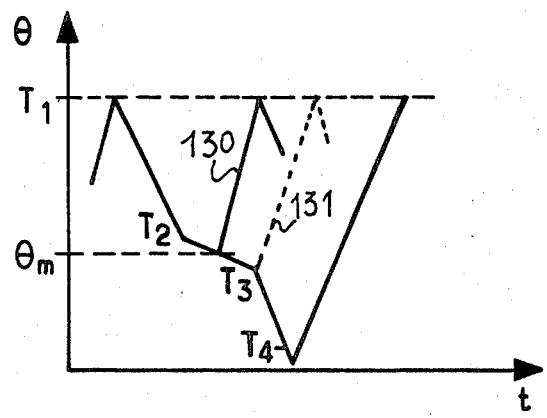
FIG. 3 is a curve representing the different possible variations of the temperature of a mirror of the hygrometer according to FIG. 2, making it possible to understand and explain the operation of the hygrometer of FIG. 2.

The hydrometer whose embodiment is shown in FIG. 2 operates in the following way; this operation will be described more particularly with reference to FIGS. 3, 4, 5A, B.

It is first of all noted that such a hygrometer as that shown in FIG. 2 operates in cyclic mode. When switched on, it starts by bringing the mirror to a temperature equivalent to temperature $T_1$, FIG. 3. At this instant, the four level comparator 43 sends to its output 45 a logic order which, through the system 49, commands the control signal generator such that the temperature regulator 57 lowers the mirror temperature very rapidly down to a temperature $T_2$, this drop in the mirror temperature being represented by the portion of the very steeply sloped curve between points $T_1$ and $T_2$ in FIG. 3. At this instant, when the temperature of the mirror $\theta$ i has reached temperature $T_2$, the four-level comparator 43 delivers at its output 46 a signal which, through the logic system 49 and the control signal generator 52 (on its input gate 51), sends an order to slow down the rate of temperature reduction of the mirror 11. The very slow rate of variation of the mirror temperature is represented by the portion of curve extending from the point marked $T_2$ in FIG. 3. From this point $T_2$, when the temperature continues to fall, but slowly, two phenomena can happen.

1. There can be the appearance of a condensate on the mirror at a temperature included between the value of temperatures $T_2$ and $T_3$. If there appears at a temperature designated as $\theta$ m a condensate on the mirror, the two-level comparator 71 delivers at its output 72 a signal which is applied to logic system 49, so as, on one hand, to keep memorised the temperature of the mirror when the first condensates appeared by commanding the sampling memory which will deliver at its output the signal of value $\theta$ m representing the temperature of commencement of condensation of the light hydrocarbons on the mirror. Furthermore, the signal obtained at the output 72 of the two-level comparator will be able to command, through logic system 49, an elevation of the mirror temperature by a logic order applied to its input 54, which will reverse the direction of command so that the mirror temperature rises again to a temperature equivalent to $T_1$, this portion of curve is shown at 130 extending from the point referenced as $\theta$ m in FIG. 3 (these results are also shown more particularly in FIG. 5A). The curve 131, in a dotted line in FIG. 3, represents the variations in the mirror temperature when the command to raise the temperature does not occur immediately after the appearance of the first condensates, but solely when the mirror temperature has reached the lowest temperature of a given range.

2. NO condensate may appear on mirror 11; then the mirror temperature drops slowly down to temperature $T_3$ (FIG. 3). From this instant, the four-level comparator 43 delivers at its output 47 a logic signal which, through the control signal generator, controls the mirror temperature regulator so as to lower the mirror temperature very rapidly to a temperature equal to $T_4$. When the mirror has reached this temperature $T_4$ (FIG. 3), the four-level comparator 43 delivers at its output 48 a signal which, through logic system 49 and the control signal generator (through its input terminal 54), will control the sense of control of the mirror temperature, making it rise again from this temperature $T_4$ to the temperature $T_1$. It is quite obvious that, nevertheless, between points $T_3$ and $T_4$ (FIG. 3) condensates can appear. In this case, the hygrometer will work in the same way as described above and the temperature $\theta$ m will be memorised in the same way as when the condensates appear between points $T_2$ and $T_3$. This temperature $\theta$ m however will be defined in a less precise way than in the preceding case.

After such a cycle, the values of the temperatures $T_2$ and $T_3$ will be adjusted automatically to the value $\theta$ m memorised, as already stated. The main aim of this adjustment is to make it easier to define the condensation temperature of the vapours contained in the carrier gas. This is more particularly advantageous in the cases of variations of concentrations of vapours of slow processes, that is to say that from one measurement to the other the temperature $\theta$ m of the start of condensation of light hydrocarbons must not vary by a large amount; that is to say that between the two measurements the vapour condensation must exhibit only a slight variation. As the temperatures $T_2$ and $T_3$ are determined from this temperature $\theta$ m, it is very likely that each time the start of condensation of the light hydrocarbons is measured, the measurement is always within the range included between $T_2$ and $T_3$ FIG. 3. It will thus be sufficient to adjust the value of the range $T_2$ and $T_3$, in particular as a function of experience. However, it is quite obvious that accidents can happen and that condensates can arrive very rapidly in large amounts; in this case, the temperature $\theta$ m may be outside this range included between $T_2$ and $T_3$, either above it or below it, and this is why it is necessary that the scanning of the whole possible temperature range should take place regardless of the result obtained, as long as the condensates have not appeared, FIG. 3, from points $T_1$ to $T_4$.

It is necessary to add that differentiator 88, when it is used in such a hygrometer, permits, by virtue of the signal delivered at its output 90, the even greater slowing of the variation in the drop in temperature of the mirror when the first condensates appear (see curve 120 in FIG. 4), in order that the temperature of the mirror does not drop too much below its temperature of start of condensation of the first light hydrocarbons contained in the gas scanning the hygrometer head 10 due to the thermal inertia of the mirror.

Lastly, when the mirror temperature again reaches temperature $T_1$, the automatic calibration circuit 62 makes it possible, during a time constant specific to it—a second, for example—to calibrate the Wheatstone bridge by actuating the electronic potentiometer 29, so that the signal delivered by the sensor is substantially zero and in any case clearly less than the level $N_f$ of FIG. 4.

Figure 5:
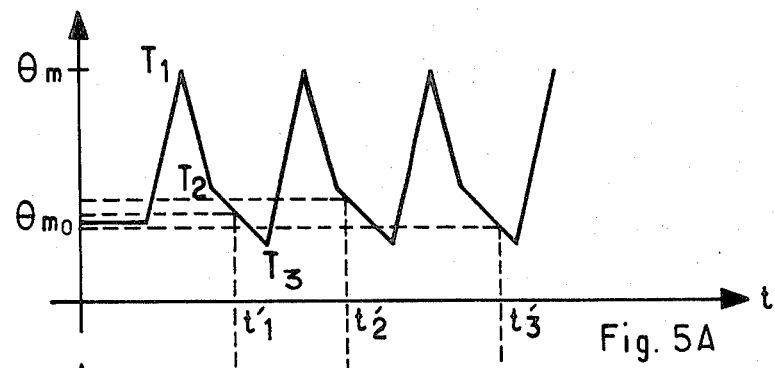
Figure 5:
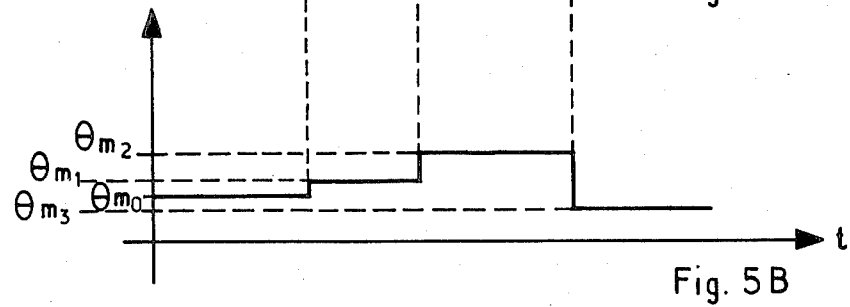

It has been mentioned above that each time the signal at the output of the sensor exceeded the operating level $N_f$, an order was sent to the sampling memory 39 such that the memory sampler 39 sampled the temperature $\theta$ i at the instant when the signal delivered by the sensor exceeded this operating level $N_f$. Thus, the output of the sampling memory delivers the value of the temperature memorised, that is to say the value $\theta$ m, which can be utilised by the technicians. FIG. 5 shows the different values of $\theta$ m for different measurements, assuming that at each passage between $T_2$ and $T_3$ light hydrocarbons have condensed.

FIG. 5A shows the temperature variations of the mirror in the case of the appearance of the condensates at each of the above-described cycles.

This FIG. 5A shows the different values $T_1$ of the maximum temperature, the value $T_2$ of the temperature from which the cooling speed is greatly reduced, and the different values of the temperature $\Theta$ m, at which the first condensates appear on the mirror.

To the instant of the different values $\theta m_1$, $\theta m_2$, $\theta m_3$, correspond a number of instants $t'_1$, $t'_2$, $T'_3$, at which instants the different values of the temperature of commencement of condensation on the mirror were memorised. FIG. 5B represents the value of the signal which can be obtained at the output of the sampling memory 39, which therefore delivers a constant signal between each instant $t'_1$, $t'_2$, $t'_3$ at which the order for memorisation of the condensation temperature m was given.

As these operating cycles are fairly fast as compared with the slow evolution, all of the constant signals represented for example in FIG. 5B by portions of curves parallel to the times axis, give a good representative value of the evolution of the different values and different concentrations of the light hydrocarbons contained in the gases to be analysed. These curves can no doubt be easily utilisable by the technicians in charge of monitoring, for example, the production of the gas flowing through the hygrometer. Furthermore, these values are really representative values of the condensation temperature of the different light hydrocarbons. These different temperature ranges, with their slow and fast variations respectively in the three ranges as defined hereinbefore, make it possible to increase the number of cycles per unit time whilst retaining a good precision of the measurement of the condensation temperature, in particular of hydrocarbons.

There has been described hereinabove a hygrometer with a more particularly advantageous application in the case of the determination of the condensation of hydrocarbons in gases. However, as has been stated, these hygrometers could be used in other fields of application; to do so, it would suffice to adapt the mirror structure and the position of the photocells depending on whether the product condensing on the mirror makes the mirror either reflective or diffusing. These modifications would, in any case, be minor as compared with the structure of the unit and above all would not remove the hygrometer from the scope of the invention.

It is also necessary to state that the hygrometer which has been described is supposed to measure gases containing vapours at slowly evolving concentrations. However, it may happen that there are moments in the operation of the hygrometer at which there will be no vapours in the gas, as for example when the measuring process is started, or else a sudden substantial change in the concentration variation—as, for example, in the case of an accident in the production of the gas. In both cases the hygrometer nevertheless gives an acceptable result.

Thus, when—at start-up—there is no vapour in the gas, a presumed condensation temperature $\theta$ m has not yet been determined. The values $T_2$ and $T_3$, FIG. 3, then have no significant value as $\theta$ m is anyway equal to the signal obtained at the output of the sampling memory, and this could be, for example, a zero value or a value included between $T_1$ and $T_4$. However, the logic system commands a cycle normally anticipated (FIG. 3) and when the first few condensates appear, regardless of the variation of the mirror temperature - slow or fast - the photocells will deliver a signal which will permit the mirror temperature at the instant when the first condensates appeared to be memorised. This temperature will be nevertheless very representative of the measurement made if it falls into the part included between the points $T_2$ and $T_3$ and the hygrometer will work perfectly. On the other hand, if this temperature falls into one of the two fast ranges, between $T_1$ and $T_2$ and between $T_3$ and $T_4$, FIG. 4, the photocells will detect a temperature which will be memorised as $\theta$ m. This temperature will perhaps not be determined with such precision as in the preceding case, but it will nevertheless be fairly close to the real value. This value will nevertheless make it possible to recenter the range $T_2$ and $T_3$ and after one or two more cycles, to obtain very good results and to have a condensation temperature centred in the range included between $T_2$ and $T_3$.

In the event that there is a sudden substantial variation in the hydrocarbon concentration, the hygrometer will react in the same way as before and only one or two measurements on one or two cycles will be able to have less precision than for the other cycles, and the range will by very rapidly centered on the presumed condensation temperature.

I claim:

1. A method of determining the temperature of the condensation point of a first substance, such as light hydrocarbons, in a gas that can contain a second and more slowly condensing substance, such as heavy hydrocarbons, the method comprising the steps of:
   (a) heating a mirror placed in an enclosure arranged for the throughflow of the gas up to a temperature at least equivalent to the evaporation temperature of both substances thought to be present in the gas;
   (b) cooling the mirror relatively quickly to a temperature slightly higher than the presumed condensation temperature for the first substance, and then continuing to cool the mirror more slowly until the appearance of the first condensates on the mirror;
   (c) storing the value of the mirror temperature at which said first condensates appear; and
   (d) repeating steps (a) to (c) using the stored temperature value as the value of the presumed condensation temperature in step (b).

2. A method according to claim 1, wherein the mirror temperature is reduced relatively rapidly to a temperature lower than the lowest possible condensation temperature for the substances thought to be present in the gas if condensates do not appear after a predetermined amount of said slower cooling of the mirror.

3. A method according to claim 1, wherein steps (a), (b) and (c) are repeated cyclically, the stored temperature value of each step (c) being used as the presumed temperature value of the subsequent step b), and wherein each step (a) is effected as a function of the determination of the mirror temperature at which the first condensates appear.

4. A method according to claim 3, wherein each step (a) is effected as soon as the first condensates appear on the mirror.

5. A method according to claim 3, wherein each step (a) is effected when the temperature of the mirror has reached a given temperature lower then the temperature at which the first condensates appeared thereon, said given temperature being the lowest temperature in a given range of temperatures.

6. A method according to claim 1,
   further including producing a signal as a function of the thickness of the condensates on the mirror.

7. A method according to claim 6, further including comparing said signal with a first level corresponding to a given thickness of condensates on the mirror.

8. A method according to claim 7, wherein, after being compared with said first level, said signal is compared with a second level corresponding to a predetermined maximum thickness of condensates on the mirror.

9. A method according to claim 7, further including triggering ana alarm if said signal has not exceeded said first level at the end of a cycle.

10. A method according to claim 8, wherein a prealarm is triggered if said signal does not exceed said second level after exceeding said first level.

11. A method according to claim 1, including memorising, for each cycle, the mirror temperature at the appearance of the first condensates.

12. A method according to claim 7, including memorising, for each cycle, the mirror temperature at the appearance of the first condensates, and determining the temperature of the mirror at the instant when said signal passes said first level.

13. Apparatus for determining the temperature of the condensation point of a first substance, such as light hydrocarbons, in a gas which can contain a second and more slowly condensing substance, such as heavy hydrocarbons, the apparatus comprising: an enclosure arranged for the throughflow of the gas; a mirror in said enclosure; means for cooling and heating the mirror so as to cause the first substance to condense on and evaporate from the mirror; means for measuring the temperature of the mirror; means for detecting the appearance of the first condensate on the mirror; logic circuit means arranged to control the heating and cooling means in response to the measuring means and the detecting means such that the mirror is heated to a temperature at least equivalent to the evaporation temperature of both substances, then cooled relatively rapidly to a temperature slightly higher than the presumed condensation temperature for the first substance, then cooled more slowly until the first condensates appear thereon; and means for storing the value of the mirror temperature at which said first condensates appear; the logic circuit means being arranged to cause the heating and cooling means to repeat said heating and cooling of the mirror at least once, the change from relatively rapid to slower cooling being effected by using said stored temperature value as said presumed condensation temperature value.

Apparatus according to claim 13, wherein said logic circuit means is arranged to cause said heating and cooling means to operate cyclically, the stored temperature value of one cycle being used as the presumed condensation temperature value of the succeeding cycle.

14. Apparatus according to claim 13, wherein said logic circuit means is arranged to cause said heating and cooling means to operate cyclically, the stored temperature value of one cycle being used as the presumed condensation temperature value of the succeeding cycle.

15. Apparatus according to claim 13, wherein the detecting means comprises electro-optical means for producing a signal as a function of the thickness of the said condensates on the said mirror.

16. Apparatus according to claim 15, wherein the detecting means further comprise means for comparing said signal with at least one level representing a predetermined thickness of condensates on the mirror.

17. Apparatus according to claim 15, wherein said electro-optical means comprise a source for emitting a light beam directed onto the said mirror, at least one photocell arranged to receive light reflected by the mirror, means responsive to the photocell to produce said signal, and means controllable to restore said signal to a reference value in the absence of condensates on the said mirror.

18. Apparatus according to claim 13, comprising means for slowing down the cooling of the said mirror at the commencement of the appearance of the said condensates on the said mirror, said slowing means co-operating with the detecting means.

19. Apparatus for determining the temperature of the condensation point of a substance in a gas, the apparatus comprising:

an enclosure arranged for the through flow of the gas;
a mirror disposed in the enclosure;
controllable means for heating the mirror;
controllable means for cooling the mirror;
a sensor for sensing the temperature of the mirror;
a controllable sampling memory whose input is connected to the output of the temperature sensor;
a first comparator having a first input connected to the output of the sampling memory and a second input connected to the output of the temperature sensor, the comparator being arranged to compare the signal delivered by the temperature sensor with predetermined values and/or values produced as a function of the signal obtained at the output of the said sampling memory;
logic circuit means having first inputs connected to the outputs of the said comparator;
a control signal generator having first inputs connected to corresponding outputs of the logic circuit means;
a temperature regulator having two inputs connected to the output of the temperature sensor and to the output of the control signal generator respectively, the output of said regulator being connected to control the said heating and/or cooling means of the mirror;
an electro-optical sensor for producing a signal indicative of the thickness of the condensates on the mirror; and
an electronic signal processing circuit for processing the signal produced by the electro-optical sensor and applying the processed signal to the said logic circuit means.

20. Apparatus according to claim 19, wherein the signal processing circuit comprises a further comparator.

21. Apparatus according to claim 20, wherein the further comparator is arranged to compare the signal produced by the electro-optical sensor with a reference level corresponding to a predetermined minimum thickness of condensates on the mirror.

22. Apparatus according to claim 21, wherein the further comparator is also arranged to compare the signal produced by the electro-optical sensor with a reference level corresponding to a predetermined maximum thickness of condensates on the mirror.

23. Apparatus according to claim 22, wherein said further comparator has first and second outputs at which it produces first and second signals respectively indicating that the condensate on the mirror has reached said predetermined minimum and maximum thicknesses respectively, the first output of the further comparator being connected to the input of a delay circuit whose output is connected to the first input of an AND gate, said AND gate having another input connected to the second output of the further comparator and an output connected to an input of the logic circuit means.

24. Apparatus according to claim 19, wherein the signal processing circuit additionally comprises a servo loop to restore the signal delivered by the electro-optical sensor to a predetermined reference level in the absence of condensate on the mirror.

25. Apparatus according to any claim 19, further comprising a differentiating circuit having its input connected to the output of the electro-optical sensor, and its output connected to a control input of the control signal generator.

* * * * *